United States Patent [19]

Borden et al.

[11] 4,454,115

[45] Jun. 12, 1984

[54] METHOD OF REDUCING THE LEVEL OF LOW DENSITY LIPOPROTEINS IN THE SERUM OF A PATIENT

[75] Inventors: Ernest C. Borden; Earl S. Shrago, both of Madison, Wis.

[73] Assignee: Wisconsin Alumni Research Foundation, Madison, Wis.

[21] Appl. No.: 314,449

[22] Filed: Oct. 23, 1981

[51] Int. Cl.³ .............................................. A61K 45/02
[52] U.S. Cl. ...................................... 424/85; 424/177; 435/811
[58] Field of Search ..................... 424/85; 435/68, 811

[56] References Cited

PUBLICATIONS

Chemical Abstracts, vol. 70, p. 201, Abst. No. 56041b, 1969.
Cantell, K. et al., New England Journal of Medicine, vol. 302, pp. 1032–1033, 1980.
Ehnholm, C. et al., Arterosclerosis, vol. 2, pp. 68–73, 1982.

Primary Examiner—Blondel Hazel
Attorney, Agent, or Firm—Howard W. Bremer

[57] ABSTRACT

A method is described for reducing the level of low density lipoproteins in the serum of a patient by administering to the patient human fibroblast interferon.

9 Claims, No Drawings

METHOD OF REDUCING THE LEVEL OF LOW DENSITY LIPOPROTEINS IN THE SERUM OF A PATIENT

This invention was made with Government support under Grant No. DHHS PHS NIH 5-P01-CA-20432-05 awarded by the Department of Health and Human Services. The Government has certain rights in this invention.

This invention relates to the medical arts and, more particularly, to an improved method for reducing the level of low density lipoproteins in the serum of a patient.

Serum lipids include free fatty acis, triglycerides, and cholesterol. Cholesterol circulates primarily as a complex of lipid and proteins. These peptides are called lipoproteins. Lipoprotein complexes can be separated, on the basis of density, into chylomicrons, low density lipoproteins, and high density lipoproteins. Serum cholesterol is found primarily in the form of low density and high density lipoproteins.

Serum cholesterol level has for some time been considered to be closely relates to arteriosclerosis. However, it is only relatively recently that the difference in the effect of high density and low density lipoproteins was noted. It is generally believed that the high density lipoproteins do not contribute to arteriosclerosis and in fact may even have an inhibitory effect on the disease. On the other hand, the level of low density lipoproteins in serum has been correlated with the disease. The distinction between low density lipoproteins and high density lipoproteins is well established among those persons skilled in the art, the dividing line typically being considered a density of 1.063 grams per cubic centimeter.

It is an object of the present invention to provide a method for reducing the level of low density lipoproteins in the serum of a patient. Other objects of the invention will become apparent to those skilled in the art from the following description.

Very generally, the method of the invention comprises administering to a patient human fibroblast interferon such as to reduce the level of low density lipoproteins in the patient's serum.

Cantell has reported noting a reduction in circulating high density lipoprotein cholesterol in three patients receiving leukocyte interferon. Naturally this is undesirable because of the possible beneficial effect of high density lipoproteins by inhibiting arteriosclerosis.

Quite unexpectedly, in connection with the present invention, it has been discovered that unlike leukocyte interferon, fibroblast interferon ($\beta$ interferon) does not reduce serum levels of high density lipoproteins. Even more importantly, fibroblast interferon does reduce serum levels of low density lipoproteins.

This effect has been demonstrated in the treatment of six female patients. These patients received daily intramuscular injections of human fibroblast interferon. No decrease in high density lipoprotein cholesterol was noted. However, by the 28th day, total cholesterol levels in the sera of all patients had dropped significantly. Since most of the remaining fraction of total cholesterol is present as low density lipoproteins, such a change indicates a decline in low density lipoprotein cholesterol resulting from the administration of fibroblast interferon.

The mean total cholesterol level and the low density lipoprotein cholesterol level (LDL) in the six patients upon initiation of fibroblast interferon administration (0), upon the 15th day and upon the 30th day were as follows:

| Study Days | Total Cholesterol | LDL Cholesterol |
|---|---|---|
| 0 | 186 mg/dl | 142 |
| 15 | 162 | 117 |
| 30 | 170 | 123 |

Dosage levels were 3 to 6 million interferon units.

In practicing the method of the invention, it is preferred that the administration of the fibroblast interferon be intramuscular and be done in a series of doses over a predetermined period of time. Such doses may be given daily, but periods of from a few hours to a few days between doses may be satisfactory depending upon the patient, the patient's tolerance to the interferon, and the beginning and desired cholesterol levels. Interferon may also be administered intravenously. Since the techniques for measuring cholesterol levels are well known in the art, monitoring can be readily accomplished in order to effect the reduction which the physician treating the patient desires. Dosage levels may be as low as one or a few million units and as high as about 30 million depending upon the interval between dosages.

It may be seen, therefore, that the invention provides an effective means of reducing the level of low density lipoproteins in the serum of a patient without affecting the level of high density lipoproteins in the patient's serum.

Various modifications of the invention in addition to those described herein will become apparent to those skilled in the art from the foregoing description. Such modifications are intended to fall within the scope of the appended claims.

What is claimed is:

1. A method for reducing the level of low density lipoproteins in the serum of a patient which comprises, administering human fibroblast interferon to the patient in an amount sufficient to lower the level of said low density lipoproteins.

2. A method according to claim 1 wherein the interferon is administered intramuscularly.

3. A method according to claim 1 wherein the interferon is administered in a plurality of doses over a predetermined period of time.

4. A method according to claim 3 wherein the interferon is administered daily.

5. A method according to claim 3 wherein the dosage level is between 3 million and 6 million units.

6. A method for reducing the level of low density lipoproteins in the serum of a patient, which comprises administering an amount of human fibroblast interferon to the patient by intramuscular injection, in a series of doses over a predetermined period of time, sufficient to lower the level of said low density lipoproteins.

7. A method according to claim 6 wherein the dosage level is between 1 million and 30 million units.

8. A method for treating arteriosclerosis in a patient, comprising, administering to said patient human fibroblast interferon in an amount sufficient to lower the level of low density lipoproteins in the patient's serum without lowering the level of high density lipoproteins in the patient's serum.

9. The method of claim 8 wherein the interferon is administered by intramuscular injection.

* * * * *